(12) United States Patent
Bobgan et al.

(10) Patent No.: US 10,617,876 B2
(45) Date of Patent: Apr. 14, 2020

(54) IMD HAVING ANTI-MIGRATION AND DEVICE EXTRACTION FEATURES

(71) Applicant: Cardiac Pacemakers, Inc., St. Paul, MN (US)

(72) Inventors: Jean M. Bobgan, Maple Grove, MN (US); David P. Stieper, North Branch, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 0 days.

(21) Appl. No.: 15/488,776

(22) Filed: Apr. 17, 2017

(65) Prior Publication Data
US 2017/0296828 A1    Oct. 19, 2017

Related U.S. Application Data

(60) Provisional application No. 62/324,234, filed on Apr. 18, 2016.

(51) Int. Cl.
| | | |
|---|---|---|
| *A61N 1/375* | (2006.01) | |
| *A61N 1/05* | (2006.01) | |
| *A61B 5/00* | (2006.01) | |
| *A61N 1/39* | (2006.01) | |

(52) U.S. Cl.
CPC ............ *A61N 1/3752* (2013.01); *A61B 5/686* (2013.01); *A61N 1/37518* (2017.08); *A61N 1/3962* (2013.01); *A61N 2001/0578* (2013.01)

(58) Field of Classification Search
CPC ................ A61N 1/3752; A61N 1/3962; A61N 1/37518; A61N 2001/0578; A61B 5/686
See application file for complete search history.

(56) References Cited

U.S. PATENT DOCUMENTS

| | | | |
|---|---|---|---|
| 8,744,572 B1 * | 6/2014 | Greenhut | A61N 1/37288 607/4 |
| 9,126,032 B2 * | 9/2015 | Khairkhahan | A61N 1/362 |
| 2007/0123923 A1 | 5/2007 | Lindstrom et al. | |
| 2009/0203953 A1 * | 8/2009 | Lamoureux | A61N 5/1027 600/8 |
| 2012/0059467 A1 * | 3/2012 | Drew | A61N 1/375 623/11.11 |

(Continued)

FOREIGN PATENT DOCUMENTS

WO       2010135440 A1    11/2010

OTHER PUBLICATIONS

Hoffstetter, Matthieu, "Medtronic cree les pacemakers du futur (Medtronic creates the pacemakers of the future)," with English translation via Google. Telemedecine, Apr. 20, 2014, 13 pages. Available online via <http://www.bilan.ch/techno-les-plus-de-la-redaction/medtronic-cree-les-pacemakers-du-futur.

(Continued)

*Primary Examiner* — Catherine M Voorhees
(74) *Attorney, Agent, or Firm* — Faegre Drinker Biddle & Reath LLP

(57) ABSTRACT

An implantable medical device comprising a housing having an outer surface; and protrusions disposed on the outer surface, where the plurality of protrusions are configured to reduce at least one of rotational, translational, and lateral movement of the implantable medical device within a patient's tissue after implantation in the patient.

16 Claims, 6 Drawing Sheets

(56) References Cited

U.S. PATENT DOCUMENTS

| | | | |
|---|---|---|---|
| 2012/0116489 A1* | 5/2012 | Khairkhahan | A61N 1/375 607/127 |
| 2014/0135882 A1 | 5/2014 | Prasannakumar et al. | |
| 2014/0163579 A1* | 6/2014 | Tischendorf | A61N 1/36139 606/129 |
| 2016/0129267 A1* | 5/2016 | Thom | A61N 1/3605 607/116 |

OTHER PUBLICATIONS

International Search Report and Written Opinion issued in PCT/US20171027874, dated Oct. 11, 2017, 12 pages.

\* cited by examiner

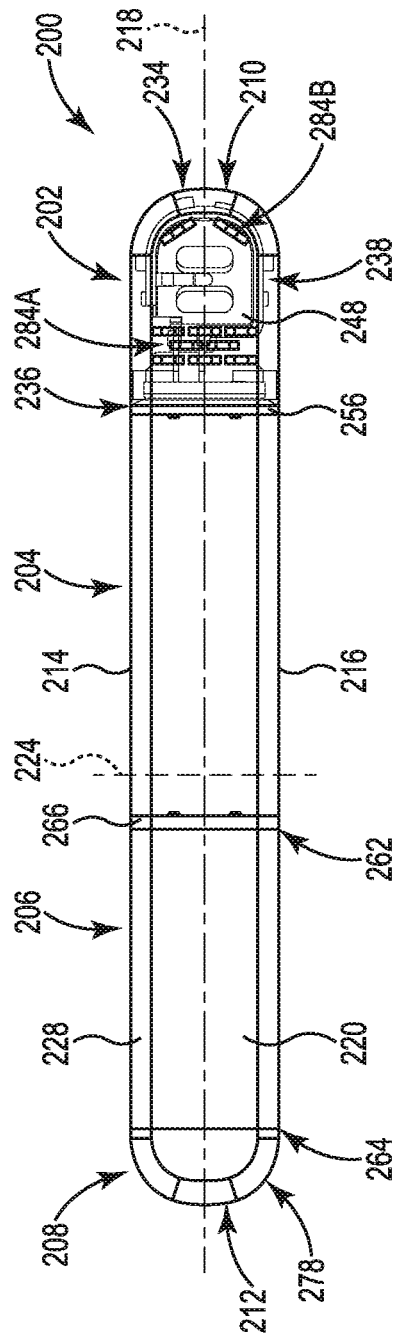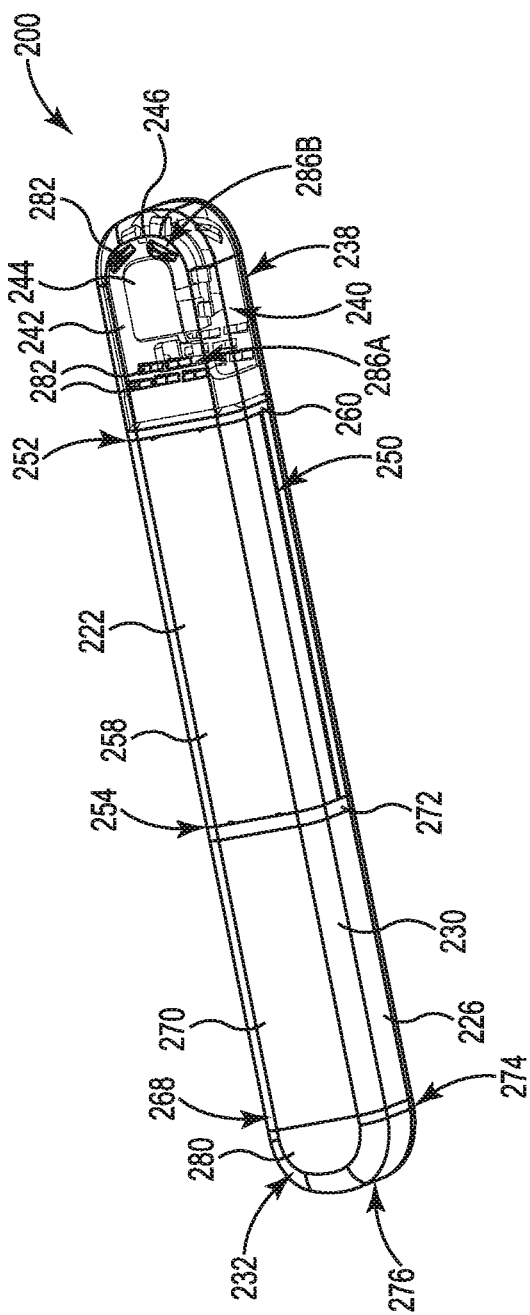

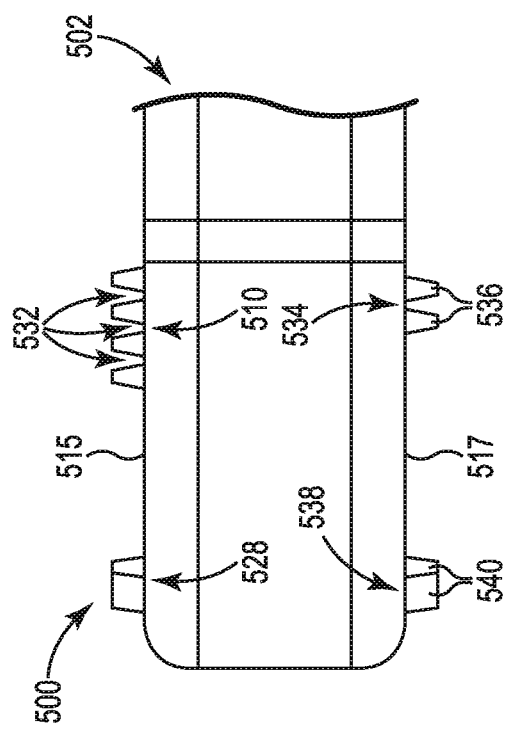
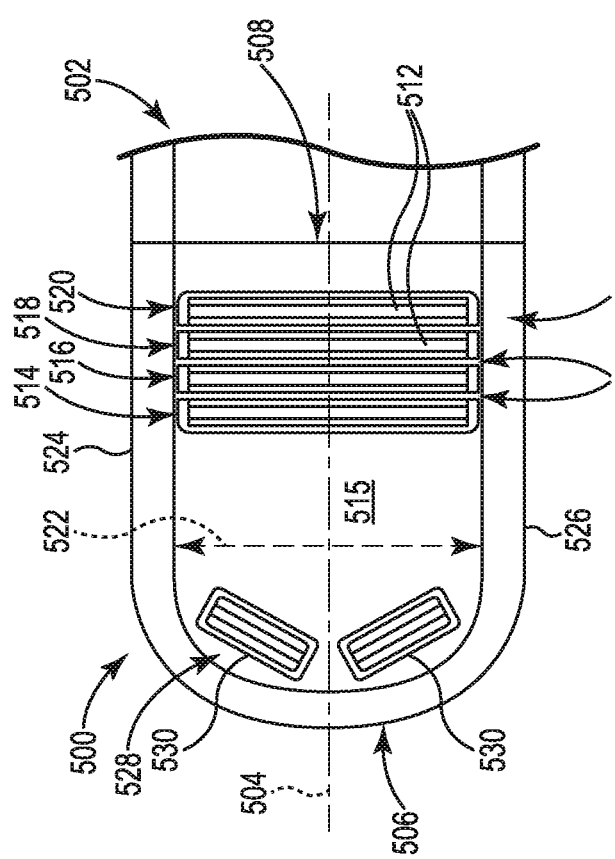
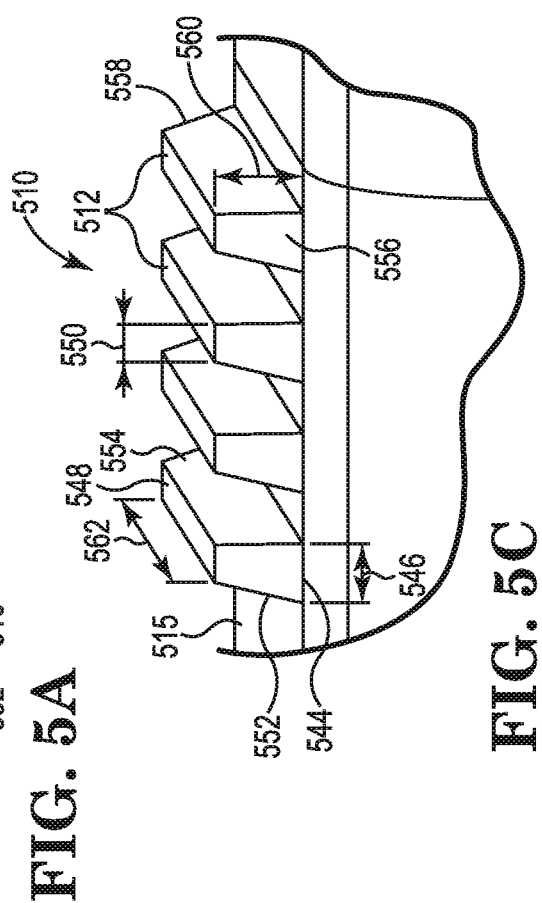

IMD HAVING ANTI-MIGRATION AND DEVICE EXTRACTION FEATURES

CROSS-REFERENCE TO RELATED APPLICATION

This application claims priority to Provisional Application No. 62/324,234, filed Apr. 18, 2016, which is herein incorporated by reference in its entirety.

TECHNICAL FIELD

Embodiments of the instant disclosure relate to medical devices and methods for reducing device migration after implantation. More particularly, the instant disclosure relates to medical devices and methods for reducing movement of a device after implantation, and to improve extraction capability.

BACKGROUND

Implantable medical devices (IMDs) may be configured to sense physiological parameters and/or provide therapy and may include one or more electrodes for performing aspects of these functions. IMDs may be implanted subcutaneously in a patient such as, for example, in a tissue pocket of the chest region. Conventional IMDs may undergo unwanted migration within the patient after implantation. Additionally, the relatively smooth external surface of conventional IMDs can frustrate the ability to grip the IMD with a medical forceps, thus making extraction of the IMD difficult.

SUMMARY

In an Example 1, an implantable medical device comprising: a housing having an outer surface; and a plurality of protrusions extending from the outer surface, wherein the plurality of protrusions are configured to reduce at least one of rotational, translational, and lateral movement of the implantable medical device within a patient's tissue after implantation in the patient.

In an Example 2, the implantable medical device of Example 1, further comprising: a core assembly comprising a core assembly housing, the core assembly having a first end and a second end; and a header coupled at a first header end to the first end of the core assembly housing, the header comprising a header housing having an outer surface extending from the first header end to a second header end.

In an Example 3, the implantable medical device of Example 2, wherein the plurality of protrusions extends from the outer surface of the header housing.

In an Example 4, the implantable medical device of Example 3, wherein the outer surface of the header housing includes a first side and a second, opposite-facing, side, the plurality of protrusions comprising a plurality of rows of protrusions, each row extending at least partially across a width of the first side, wherein each of the plurality of rows of protrusions includes at least one protrusion.

In an Example 5, the implantable medical device of Example 4, the plurality of protrusions comprising at least one additional row of protrusions disposed on the second side.

In an Example 6, the implantable medical device of either of Examples 4 or 5, wherein each of the plurality of rows of protrusions is oriented parallel to a first axis, wherein the first axis is perpendicular to a second axis, the second axis comprising an axis of symmetry of the header, extending from the first header end to the second header end.

In an Example 7, the implantable medical device of any of Examples 4-6, wherein each of the plurality of rows of protrusions is arranged to be offset from an adjacent row of protrusions.

In an Example 8, the implantable medical device of either of Examples 6 or 7, further comprising an elongated protrusion oriented at an angle to the second axis.

In an Example 9, the implantable medical device of any of Examples 1-8, wherein at least one protrusion of the plurality of protrusions has an elongated truncated pyramid shape.

In an Example 10, the implantable medical device of any of Examples 1-8, wherein at least one protrusion of the plurality of protrusions has a truncated triangular prism shape.

In an Example 11, the implantable medical device of any of Examples 1-10, wherein the plurality of protrusions are shaped to provide a complementary fit to a plurality of teeth of a medical forceps.

In an Example 12, a method of forming an implantable medical device, the method comprising: forming a core assembly comprising a core assembly housing, the core assembly having an outer surface extending between a first end and a second end; forming a header, the header comprising a header housing having an outer surface extending from a first header end to a second header end; forming a plurality of protrusions disposed on the outer surface of the header housing; and coupling the header, at a second header end, to the first end of the core assembly housing.

In an Example 13, the method of Example 12, wherein the outer surface of the header housing includes a first side and a second, opposite-facing, side, and wherein forming the plurality of protrusions comprises forming a plurality of rows of protrusions, each row extending at least partially across a width of the first side, wherein each of the plurality of rows of protrusions includes at least one protrusion, wherein each of the plurality of rows of protrusions is aligned parallel to a first axis, and wherein the first axis is perpendicular to a second axis, the second axis comprising an axis of symmetry of the header, extending from the first header end to the second header end.

In an Example 14, the method of Example 13, wherein forming the plurality of protrusions further comprises forming an elongated protrusion oriented at an angle to the second axis.

In an Example 15, the method of any of Examples 12-14, wherein forming the plurality of protrusions comprises shaping the plurality of protrusions to provide a complementary fit to a plurality of teeth of a standard medical forceps.

In an Example 16, an implantable medical device comprising: a core assembly housing having an outer surface; a header housing coupled to the core assembly housing, the header housing having an outer surface extending from a first header end to a second header end; and a plurality of protrusions disposed on at least one of the outer surface of the header housing and the outer surface of the core assembly housing, wherein at least one of the plurality of protrusions has at least one of an elongated shape and an edge.

In an Example 17, the implantable medical device of Example 16, wherein the plurality of protrusions extends from the outer surface of the header housing.

In an Example 18, the implantable medical device of Example 17, wherein the outer surface of the header housing includes a first side and a second, opposite-facing, side, the plurality of protrusions comprising a plurality of rows of protrusions, each row extending at least partially across a width of the first side, wherein each of the plurality of rows of protrusions includes at least one protrusion.

In an Example 19, the implantable medical device of Example 18, the plurality of protrusions comprising at least one additional row of protrusions disposed on the second side.

In an Example 20, the implantable medical device of Example 18, wherein each of the plurality of rows of protrusions is aligned parallel to a first axis, wherein the first axis is perpendicular to a second axis, the second axis comprising an axis of symmetry of the header, extending from the first header end to the second header end.

In an Example 21, the implantable medical device of Example 20, wherein each of the plurality of rows of protrusions is arranged to be offset from an adjacent row of protrusions.

In an Example 22, the implantable medical device of Example 20, further comprising an elongated protrusion oriented at an angle to the second axis.

In an Example 23, the implantable medical device of Example 16, wherein at least one protrusion of the plurality of protrusions has an elongated truncated pyramid shape.

In an Example 24, the implantable medical device of Example 16, wherein at least one protrusion of the plurality of protrusions has a truncated triangular prism shape.

In an Example 25, the implantable medical device of Example 16, wherein the plurality of protrusions are shaped to provide a complementary fit to a plurality of teeth of a medical forceps.

In an Example 26, the implantable medical device of Example 16, wherein the protrusions are configured to reduce at least one of rotational, translational, and lateral movement of the implantable medical device within a patient's tissue after implantation in the patient.

In an Example 27, an implantable medical device comprising: a core assembly comprising a core assembly housing, the core assembly having a first end and a second end; a header coupled at a first header end to the first end of the core assembly housing, the header comprising a header housing having an outer surface extending from the first header end to a second header end; and a plurality of protrusions disposed on the outer surface of the header housing, wherein at least one of the plurality of protrusions has at least one of an elongated shape and an edge.

In an Example 28, the implantable medical device of Example 27, wherein the outer surface of the header housing includes a first side and a second, opposite-facing, side, the plurality of protrusions comprising a plurality of rows of protrusions, each row extending at least partially across a width of the first side, wherein each of the plurality of rows of protrusions includes at least one protrusion, wherein each of the plurality of rows of protrusions is aligned parallel to a first axis, and wherein the first axis is perpendicular to a second axis, the second axis comprising an axis of symmetry of the header, extending from the first header end to the second header end.

In an Example 29, the implantable medical device of Example 28, further comprising an elongated protrusion oriented at an angle to the second axis.

In an Example 30, the implantable medical device of Example 27, wherein the plurality of protrusions are shaped to provide a complementary fit to a plurality of teeth of a medical forceps.

In an Example 31, a method of forming an implantable medical device, the method comprising: forming a core assembly comprising a core assembly housing, the core assembly having an outer surface extending between a first end and a second end; forming a header, the header comprising a header housing having an outer surface extending from a first header end to a second header end; forming a plurality of protrusions disposed on the outer surface of the header housing, wherein at least one of the plurality of protrusions has at least one of an elongated shape and an edge; and coupling the header, at a first header end, to the first end of the core assembly housing.

In an Example 32, the method of Example 31, wherein the outer surface of the header housing includes a first side and a second, opposite-facing, side, and wherein forming the plurality of protrusions comprises forming a plurality of rows of protrusions, each row extending at least partially across a width of the first side, wherein each of the plurality of rows of protrusions includes at least one protrusion, wherein each of the plurality of rows of protrusions is aligned parallel to a first axis, and wherein the first axis is perpendicular to a second axis, the second axis comprising an axis of symmetry of the header, extending from the first header end to the second header end.

In an Example 33, the method of Example 32, wherein forming the plurality of protrusions further comprises forming an elongated protrusion oriented at an angle to the second axis.

In an Example 34, the method of Example 31, wherein at least one protrusion of the plurality of protrusions has at least one of an elongated truncated pyramid shape and a truncated triangular prism shape.

In an Example 35, the method of Example 31, wherein forming the plurality of protrusions comprises shaping the plurality of protrusions to provide a complementary fit to a plurality of teeth of a standard medical forceps.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIG. 2A is an upper view of an implantable medical device (IMD), in accordance with embodiments of the disclosure.

FIG. 2B is a lower perspective view of the IMD depicted in FIG. 2A, in accordance with embodiments of the disclosure.

FIG. 5A is a top view of an IMD header, in accordance with embodiments of the disclosure.

FIG. 5B is a side view of the IMD header depicted in FIG. 5A, in accordance with embodiments of the disclosure.

FIG. 5C is an expanded perspective view of a portion of the IMD header depicted in FIGS. 5A and 5B, in accordance with embodiments of the disclosure.

Figure 1:
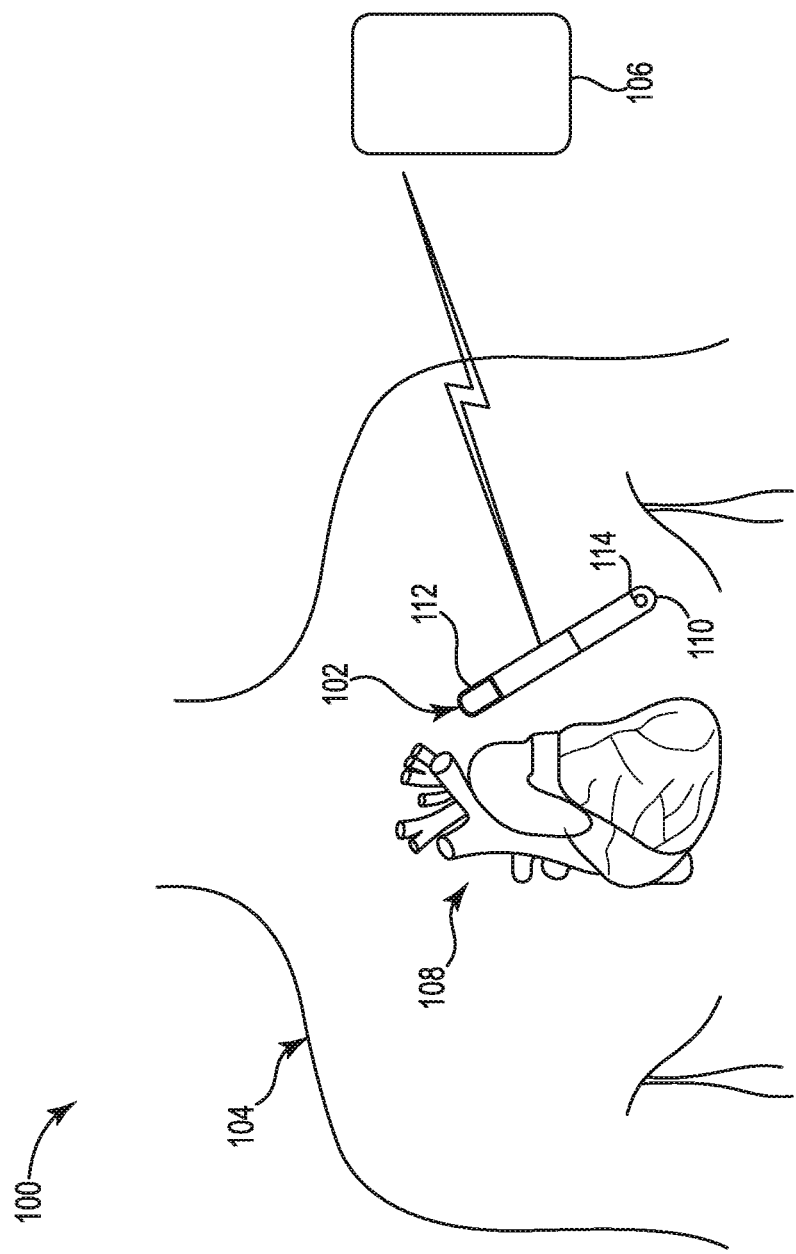
FIG. 1 is a schematic illustration of a system including an implantable medical device (IMD), in accordance with embodiments of the disclosure.

While the disclosed subject matter is amenable to various modifications and alternative forms, specific embodiments have been shown by way of example in the drawings and are described in detail below. The intention, however, is not to limit the disclosed subject matter to the particular embodiments described. On the contrary, the disclosed subject matter is intended to cover all modifications, equivalents, and alternatives falling within the scope of the disclosed subject matter as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

FIG. 1 is a schematic illustration of a system 100 including an implantable medical device (IMD) 102 implanted within a patient's body 104 and configured to communicate with a receiving device 106. In embodiments, the IMD 102 may be implanted subcutaneously within an implantation location or pocket in the patient's chest or abdomen and may be configured to monitor (e.g., sense and/or record) physiological parameters associated with the patient's heart 108. In some embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac activation signals, heart sounds, blood pressure measurements, oxygen saturations, and/or the like. In some embodiments, the IMD 102 may be configured to monitor physiological parameters that may include one or more signals indicative of a patient's physical activity level and/or metabolic level, such as an acceleration signal. In some embodiments, the IMD 102 may be configured to monitor physiological parameters associated with one or more other organs, systems, and/or the like. The IMD 102 may be configured to sense and/or record at regular intervals, continuously, and/or in response to a detected event. In embodiments, such a detected event may be detected by one or more sensors of the IMD 102, another IMD (not shown), an external device (e.g., the receiving device 106), and/or the like. In addition, the IMD 102 may be configured to detect a variety of physiological signals that may be used in connection with various diagnostic, therapeutic, and/or monitoring implementations.

For example, the IMD 102 may include sensors or circuitry for detecting respiratory system signals, cardiac system signals, and/or signals related to patient activity. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

For purposes of illustration, and not of limitation, various embodiments of devices that may be used to record physiological parameters in accordance with the present disclosure are described herein in the context of IMDs that may be implanted under the skin in the chest region of a patient. In embodiments, however, the IMD 102 may include any type of IMD, any number of different components of an implantable system, and/or the like having a housing and being configured to be implanted in a patient's body 104. For example, the IMD 102 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the patient's body and/or the IMD 102. In various embodiments, the IMD 102 may include both defibrillation and pacing/CRT capabilities (e.g., a CRT-D device).

As shown, the IMD 102 may include a housing 110 having two electrodes 112 and 114 coupled thereto. According to embodiments, the IMD 102 may include any number of electrodes (and/or other types of sensors such as, e.g., thermometers, barometers, pressure sensors, optical sensors, motion sensors, and/or the like) in any number of various types of configurations, and the housing 110 may include any number of different shapes, sizes, and/or features. In embodiments, the IMD 102 may be configured to sense physiological parameters and record the physiological parameters. For example, the IMD 102 may be configured to activate (e.g., periodically, continuously, upon detection of an event, and/or the like), record a specified amount of data (e.g., physiological parameters) in a memory, and communicate that recorded data to a receiving device 106. In the case of an IDM, for example, the IMD 102 may activate, record cardiac signals for a certain period of time, deactivate, and activate to communicate the recorded signals to the receiving device 106.

In various embodiments, the receiving device 106 may be, for example, a programmer, controller, patient monitoring system, and/or the like. Although illustrated in FIG. 1 as an external device, the receiving device 106 may include an implantable device configured to communicate with the IMD 102 that may, for example, be a control device, another monitoring device, a pacemaker, an implantable defibrillator, a cardiac resynchronization therapy (CRT) device, and/or the like, and may be an implantable medical device known in the art or later developed, for providing therapy and/or diagnostic data about the patient and/or the IMD 102. In various embodiments, the IMD 102 may be a pacemaker, an implantable cardioverter defibrillator (ICD) device, or a cardiac resynchronization therapy (CRT) device. In various embodiments, the IMD 102 may include both defibrillation and pacing/CRT capabilities (e.g., a CRT-D device).

The system 100 may be used to implement coordinated patient measuring and/or monitoring, diagnosis, and/or therapy in accordance with embodiments of the disclosure. The system 100 may include, for example, one or more patient-internal medical devices, such as an IMD 102, and one or more patient-external medical devices, such as receiving device 106. In embodiments, the receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

In embodiments, the IMD 102 and the receiving device 106 may communicate through a wireless link. For example, the IMD 102 and the receiving device 106 may be coupled through a short-range radio link, such as Bluetooth, IEEE 802.11, and/or a proprietary wireless protocol. The communications link may facilitate uni-directional and/or bi-directional communication between the IMD 102 and the receiving device 106. Data and/or control signals may be transmitted between the IMD 102 and the receiving device 106 to coordinate the functions of the IMD 102 and/or the receiving device 106. In embodiments, patient data may be downloaded from one or more of the IMD 102 and the receiving device 106 periodically or on command. The physician and/or the patient may communicate with the IMD 102 and the receiving device 106, for example, to acquire patient data or to initiate, terminate, or modify recording and/or therapy.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

FIG. 2A is an upper view of an implantable medical device (IMD) 200, and FIG. 2B is a lower perspective view of the IMD 200, in accordance with embodiments of the disclosure. The IMD 200 may be, or may be similar to, the IMD 102 depicted in FIG. 1. As shown in FIG. 2A, the IMD 200 has a header 202, a core assembly 204, a battery assembly 206, and an electrode assembly 208.

As shown in FIGS. 2A and 2B, the IMD 200 may have an elongated shape having a first end 210 and a second end 212. The IMD 200 includes a first side 214 and a second side 216. The IMD 200 may include a central axis 218 of symmetry extending along the length of the IMD 200. The IMD 200 includes a first surface 220 defined between the first end 210 and the second end 212 and between the first side 214 and the second side 216, and a second surface 222 that is opposite the first surface 220. In embodiments, the first surface 220 and/or the second surface 222 may be at least approximately planar, and the first surface 220 may be at least approximately parallel to the second surface 222. That is, for example, the first surface 220 may be disposed in a first plane and the second surface 222 may be disposed in a second plane that is parallel to the first plane. In embodiments, a second axis 224 may be defined perpendicular to the central axis 218, and disposed in a plane that is parallel to each of the first and second surfaces 220 and 222.

As shown in FIG. 2B, the IMD 200 has a third surface 226 extending along the perimeter of the IMD 200 and oriented at least approximately perpendicularly to the first and second surfaces 220 and 222. As shown, the third surface 226 includes the first and second sides 214 and 216 of the IMD 200. A fourth, curved, surface 228 extends along the perimeter of the IMD 200 and between the first surface 220 and the third surface 226. A fifth, curved, surface 230 extends along the perimeter of the IMD 200 and between the second surface 222 and the third surface 226.

In the embodiments shown in FIGS. 2A and 2B, the first surface 220 and second surface 222 are at least approximately planar and at least approximately rectangular, having rounded corners, and the third surface 226 is at least approximately planar along the first side 214 and the second side 216. In embodiments, the first surface 220 and/or second surface 222 may be at least approximately elliptical, may be curved (as opposed to planar), may have unrounded corners, or may be defined according to any number of other shapes. Similarly, in embodiments, the third surface 226, fourth surface 228, and/or fifth surface 230 may be rounded (e.g., convex or concave), at least approximately planar, or may be defined according to any number of other shapes. The first surface 220, second surface 222, third surface 226, fourth surface 228, and fifth surface 230, define an outer surface 232 of the IMD 200. In embodiments, the outer surface 232 of the IMD 200 may be defined according to any number of different shapes.

As shown in FIGS. 2A and 2B, in embodiments, the header 202 (which is illustrated as being transparent) is arranged at or near the first end 210 of the IMD 200, and includes a first end 234 and a second end 236. The header 202 includes a header housing 238 that encloses an interior region 240. As shown, an external surface 242 of the header housing 238 forms a portion of the outer surface 232 of the IMD 200. That is, for example, a portion of one or more of the first surface 220, the second surface 222, the third surface 226, the fourth surface 228, and the fifth surface 230 may be provided by the external surface 242 of the header housing 238. The header 202 may house various circuitry components within its interior region 240 (e.g., an electrode 244 and an antenna 246) positioned and supported by a scaffold assembly 248. In some embodiments, the first end 234 of the header 202 forms the first end 210 of the IMD 200.

The core assembly 204 includes core circuitry enclosed within a core assembly housing 250, and includes a first end 252 and a second end 254. The first end 252 of the core assembly 204 is coupled to the second end 236 of the header 202. In embodiments, the core assembly 204 may be coupled to the header 202 via a feed-through assembly 256, which may be configured to provide a throughput for connections configured to connect the circuitry components of the header 202 to the core circuitry disposed within the core assembly 204. As shown, an external surface 258 of the core assembly housing 250 forms a portion of the outer surface 232 of the IMD 200. That is, for example, a portion of one or more of the first surface 220, the second surface 222, the third surface 226, the fourth surface 228, and the fifth surface 230 may be provided by the external surface 258 of the core assembly housing 250. Additionally, an external surface 260 of the feed-through assembly 256 may form a portion of the outer surface 232 of the IMD 200.

The battery assembly 206 (which may include one or more batteries) includes a first end 262 coupled to the second end 254 of the core assembly 204, and a second end 264. In embodiments, the battery assembly 206 may be coupled to the core assembly 204 via a feed-through assembly 266, which may be configured to provide a throughput for connections configured to connect the circuitry components of the core assembly 204 to the one or more batteries disposed within the battery assembly 206. The battery assembly 206 includes a battery assembly housing 268, and, as shown, an external surface 270 of the battery assembly housing 268 forms a portion of the outer surface 232 of the IMD 200. That is, for example, a portion of one or more of the first surface 220, the second surface 222, the third surface 226, the fourth surface 228, and the fifth surface 230 may be provided by the external surface 270 of the battery assembly housing 268. Additionally, an external surface 272 of the feed-through assembly 266 may form a portion of the outer surface 232 of the IMD 200.

As shown, the electrode assembly 208 may form the second end 212 of the IMD 200, and may be coupled to the second end 264 of the battery assembly 206. The electrode assembly 208 may include a first end 274 and a second end 276. The electrode assembly 208 includes an electrode assembly housing 278, and, as shown, an external surface 280 of the electrode assembly housing 278 forms a portion of the outer surface 232 of the IMD 200. That is, for example, a portion of one or more of the first surface 220, the second surface 222, the third surface 226, the fourth surface 228, and the fifth surface 230 may be provided by the external surface 280 of the electrode assembly housing 278. According to embodiments, the external surface 280 of the electrode assembly housing 278 may be, or include, an electrode. In embodiments, the electrode assembly 208 may be an electrode that is disposed over an end portion of the battery assembly housing 268, which may extend to the second end 212 of the IMD 200.

As shown in FIGS. 2A and 2B, the outer surface 232 of the IMD 200 may incorporate or include additional features and structures such as, for example, protrusions 282 configured to inhibit migration of the IMD 200 within the patient's body, to facilitate gripping of the IMD 200 with a medical forceps, and/or the like. For example, the outer surface 232 of the IMD 200 may include any number of different types of protrusions 282 oriented in any number of different configurations, and having any number of different shapes. In the embodiments shown in FIGS. 2A and 2B, for example, protrusions 282 are disposed on the first surface 220 and the second surface 222. In embodiments, the IMD 200 may include one or more protrusions 282 at any other location or locations on the outer surface 232 of the IMD 200 such as, for example, on the first surface 220, the second surface 222, the third surface 226, the fourth surface 228, and/or the fifth surface 230.

According to embodiments, the IMD 200 may include at least one protrusion that has an elongated shape, as described herein, or includes at least one edge. That is, for example, the IMD 200 may include at least one protrusion that has an irregular shape, an elliptical shape, a rectangular shape, a triangular shape, and/or the like. The edge may include any type of intersection between two surfaces that may not be rounded, and may include a dull edge, a sharp edge, a beveled edge, a stepped edge, and/or the like. The edge may be characterized by any number of different angles of intersection, and may include a round edge (e.g., an edge at the intersection of a wall and a base of a truncated conical prism).

As depicted in FIGS. 2A and 2B, a first set 284A of protrusions 282 is disposed on the first surface 220 (on the external surface 242 of the header housing 238), near the second end 236 of the header 202; and a second set 284B of protrusions 282 is disposed on the first surface 220 (on the external surface 242 of the header housing 238), near the first end 234 of the header 202. Similarly, a third set 286A of protrusions 282 is disposed on the second surface 222 (on the external surface 242 of the header housing 238), near the second end 236 of the header 202; and a fourth set 286B of protrusions 282 is disposed on the second surface 222 (on the external surface 242 of the header housing 238), near the first end 234 of the header 202. According to embodiments, the first set 284A, second set 284B, third set 286A, and fourth set 286B of protrusions 282 each may include one or more protrusions 282 arranged in proximity to each other and oriented in any number of different configurations. Additionally, or alternatively, the IMD 200 may include any number of sets of protrusions (e.g., one set of protrusions, two sets of protrusions, three sets of protrusions, five sets of protrusions, etc.).

As shown, for example, the first set 284A of protrusions 282 includes three rows of protrusions 282, each row extending at least partially across a width of the first surface 220, and oriented perpendicularly to the first axis 218 (and, e.g., parallel to the second axis 224). A first row (e.g., the row closest to the first end 234 of the IMD 200) of the first set 284A of protrusions 282 includes three protrusions 282, a second row (e.g., the row adjacent the first row) includes two protrusions 282, and a third row (e.g., the row farthest from the first end 234 of the IMD 200) includes three protrusions 282. The second row is offset from the first and third rows. In other embodiments, the rows may not be offset, thereby forming a number of columns, which may, for example, be oriented parallel to the first axis 218. In embodiments, the first set 284A of protrusions 282 may include any number of rows and/or columns, any number of offset rows, and/or the like. Additionally, each row and/or column of protrusions 282 of the first set 284A may include any number of protrusions 282 (e.g., one protrusion, two protrusions, three protrusions, four protrusions, etc.). Although all of the protrusions 282 of the first set 284A of protrusions are illustrated as having the same size, shape, and orientation, in embodiments, any one or more of the size, shape, and orientation of protrusions 282 within a set, row, and/or column, may include any number of variances.

The second set 284B of protrusions 282 includes two protrusions 282, each protrusion 282 oriented differently than the other, and each protrusion 282 oriented differently than the protrusions 282 in the first set 284A. In embodiments, the second set 284B of protrusions 282 may include any number of rows and/or columns, any number of offset rows, and/or the like. Additionally, each row and/or column of protrusions 282 of the second set 284B may include any number of protrusions 282 (e.g., one protrusion, two protrusions, three protrusions, four protrusions, etc.).

As shown, for example, the third set 286A of protrusions 282 includes two rows of protrusions 282, each row extending at least partially across a width of the second surface 220, and oriented perpendicularly to the first axis 218 (and, e.g., parallel to the second axis 224). A first row (e.g., the row closest to the first end 234 of the IMD 200) of the third set 286A of protrusions 282 includes two protrusions 282, and a second row (e.g., the row adjacent the first row)

includes three protrusions 282. The second row is offset from the first row. In other embodiments, the rows may not be offset, thereby forming a number of columns, which may, for example, be oriented parallel to the first axis 218. In embodiments, the third set 286A of protrusions 282 may include any number of rows and/or columns, any number of offset rows, and/or the like. Additionally, each row and/or column of protrusions 282 of the third set 286A may include any number of protrusions 282 (e.g., one protrusion, two protrusions, three protrusions, four protrusions, etc.). Although all of the protrusions 282 of the third set 286A of protrusions are illustrated as having the same size, shape, and orientation, in embodiments, any one or more of the size, shape, and orientation of protrusions 282 within a set, row, and/or column, may include any number of variances.

The fourth set 286B of protrusions 282 includes two protrusions 282, each protrusion 282 oriented differently than the other, and each protrusion 282 oriented differently than the protrusions 282 in the third set 286A. In embodiments, the fourth set 286B of protrusions 282 may include any number of rows and/or columns, any number of offset rows, and/or the like. Additionally, each row and/or column of protrusions 282 of the fourth set 286B may include any number of protrusions 282 (e.g., one protrusion, two protrusions, three protrusions, four protrusions, etc.).

According to various embodiments, protrusions may be arranged in rows that are aligned to form multiple longitudinal columns of at least two protrusions. As shown in FIGS. 2A and 2B, the protrusions may be arranged in multiple rows, where each row is offset from an adjacent row. In embodiments, a set of protrusions may include a number of rows, with each of the rows of protrusions aligned at least approximately perpendicular to the central axis 218, at least approximately parallel to the central axis 218, and/or at an angle to the central axis 218. Any other arrangement of protrusions, rows of protrusions, columns of protrusions, and/or the like, may be implemented in accordance with embodiments of the disclosure. The protrusions may be formed according to any number of different shapes. For example, each protrusion may have a triangular cross sectional shape, having for example a widened base attached to the outer surface 232 of the IMD 200 and a narrowed apex, truncated side, or peak. In embodiments, each protrusion may have a truncated pyramid shape, a truncated triangular prism shape, a block shape, a cylindrical shape, or any three dimensional shape. In embodiments, each protrusion may have any number of different sizes, and in embodiments, the protrusions may be sized to fit within the grip of a medical forceps, as shown, for example, in FIG. 3.

Figure 3:
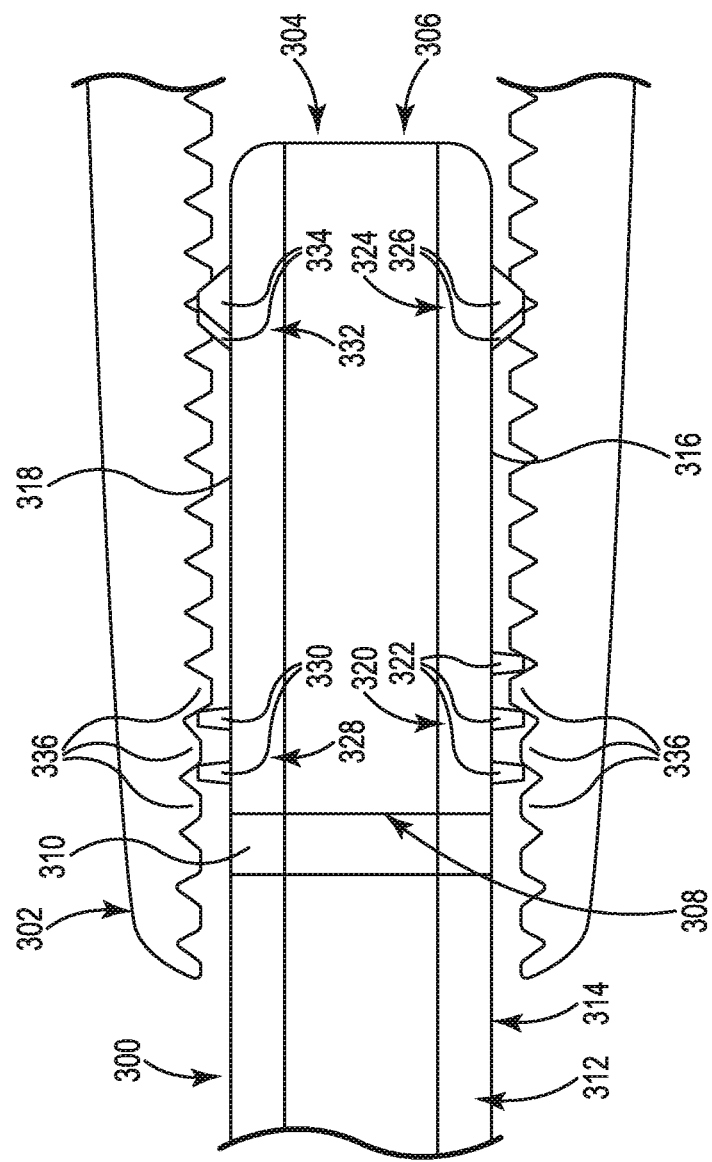
FIG. 3 is a side view of a portion of an IMD being gripped by a portion of a medical forceps, in accordance with embodiments of the disclosure.

FIG. 3 is a side view of a portion of an IMD 300 being gripped by a portion of a medical forceps 302, in accordance with embodiments of the disclosure. The IMD 300 may be, be identical to, or be similar to, the IMD 102 depicted in FIG. 1 and/or the IMD 200 depicted in FIGS. 2A and 2B. As shown, for example, in FIG. 3, the IMD 300 includes a header 304 having a first end 306 and a second end 308. The second end 308 of the header 304 is coupled, via a feedthrough assembly 310 to a core assembly 312. As shown in FIG. 3, the IMD 300 includes an outer surface 314, which includes a first surface 316 and a second, opposite and parallel, surface 318.

A first set 320 of protrusions 322 is disposed on the first surface 316 near the second end 308 of the header 304; a second set 324 of protrusions 326 is disposed on the first surface 316 near the first end 306 of the header; a third set 328 of protrusions 330 is disposed on the second surface 318 near the second end 308 of the header; and a fourth set 332 of protrusions 334 is disposed on the second surface 318 near the first end 306 of the header 304. As shown, the protrusions 322, 326, 330, and 334 are shaped and arranged to correspond to the shape and arrangement, respectively, of the teeth 336 of the medical forceps 302. For example, the width of each protrusion may be sized to fit within each of the spaces in the grips of a medical forceps; and the height of each protrusion may be sized to be received a distance into the grip of a medical forceps. In embodiments, the protrusions 322, 326, 330, and 334 may be sized with a complementary height, length, and/or width to the teeth 336 of a standard medical forceps, a custom medical forceps, and/or the like. In embodiments, the protrusions 322, 326, 330, and 334 may be configured in different sizes so that at least one of the protrusions 322, 326, 330, and 334 corresponds to one of several different styles, sizes, and/or shapes of forceps. In embodiments, for example, the protrusions maybe shaped to correspond to a medical forceps having a grid patterned grip, a checkered grip, a number of rows of teeth, and/or any suitable pattern for gripping or holding.

Figure 4A:
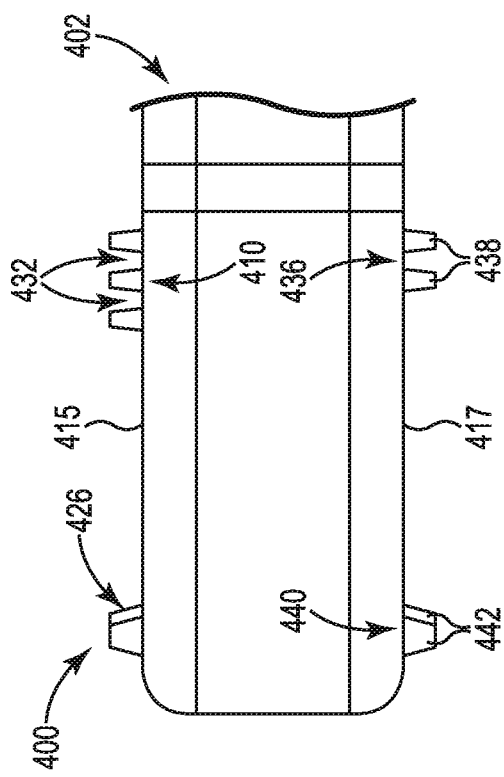
FIG. 4A is a top view of an IMD header, in accordance with embodiments of the disclosure.

FIG. 4A is a top view of a header 400 of an IMD 402, in accordance with embodiments of the disclosure. The IMD 402 may be, be identical to, or be similar to, the IMD 102 depicted in FIG. 1, the IMD 200 depicted in FIGS. 2A and 2B, and/or the IMD 300 depicted in FIG. 3. A central axis 404 of symmetry extends along the length of the IMD 402, from a first end 406 of the header 400 to a second end 408 of the header 400, as shown.

A first set 410 of protrusions 412 is arranged, on a first surface 415 (which forms a portion of an outer surface of the IMD 402), near the second end 408 of the header 400. As shown in FIG. 4A, the first set 410 of protrusions 412 is arranged in three rows 414, 416, and 418. Each row 414, 416, and 418 is oriented perpendicular to the central axis 404 and extends partially across a width 420 of the header 400, defined between a first side 422 and a second side 424. The first row 414 includes three protrusions 412, the second row 416 includes two protrusions 412, and the third row 418 includes three protrusions 412. The second row 416 is offset from the first and third rows 414 and 418. In other embodiments, the rows 414, 416, and 418 may not be offset, thereby forming a number of columns, which may, for example, be oriented parallel to the central axis 404. In embodiments, the first set 410 of protrusions 412 may include any number of rows and/or columns, any number of offset rows, and/or the like. Additionally, each row and/or column of protrusions 412 of the first set 410 may include any number of protrusions 412 (e.g., one protrusion, two protrusions, three protrusions, four protrusions, etc.). Although all of the protrusions 412 of the first set 410 are illustrated as having the same size, shape, and orientation, in embodiments, any one or more of the size, shape, and orientation of protrusions 412 within a set, row, and/or column, may include any number of variances. For example, each of the protrusions 412 may have a truncated pyramid shape, a truncated triangular prism shape, a block shape, a cylindrical shape, and/or any other suitable three-dimensional shape.

Figure 4B:
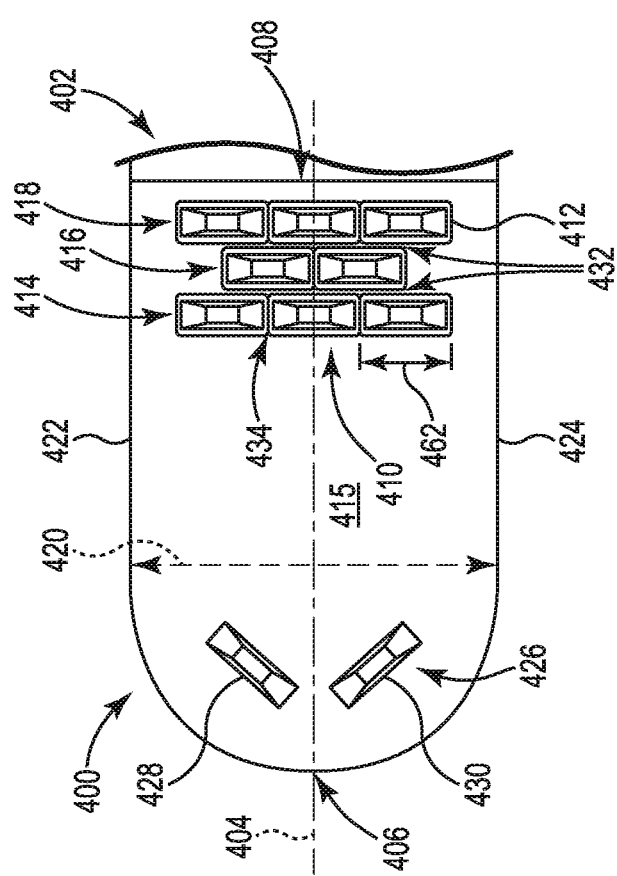
FIG. 4B is a side view of the IMD header depicted in FIG. 4A, in accordance with embodiments of the disclosure.

In the illustrated embodiments, and as also shown in FIG. 4B, there may be a space 432 defined between the rows of each set of adjacent rows 414, 416, and 418. The space 432 may be sized to receive corresponding teeth of a medical forceps. In embodiments, each row 414, 416, and 418 of protrusions 412 may have a space 434 between adjacent protrusions 412 within the same row. The size and shape of each space 434 may also be sized to receive corresponding teeth of a medical forceps.

As shown in FIG. 4A, the header 400 includes a second set 426 of protrusions 428 and 430, arranged near the first end 406 of the header 400. Each of the protrusions 428 and 430 of the second set 426 is oriented at an angle to the central axis 404 of the IMD 402. As shown in FIG. 4A, the second set 426 of protrusions 428 and 430 includes two protrusions 428 and 430, each oriented at an angle to the other. In other embodiments, one or more of the protrusions 428 and 430 of the second set 426 may be parallel or perpendicular to the central axis 404 of the IMD 402. In embodiments, the second set 426 of protrusions 428 and 430 may include any number of protrusions, arranged in any number of different orientations, rows and/or columns, any number of offset rows, and/or the like. Additionally, each row and/or column of protrusions 428 and 430 of the second set 426 may include any number of protrusions 428, 430 (e.g., one protrusion, two protrusions, three protrusions, four protrusions, etc.). Although both of the protrusions 428 and 430 of the second set 426 are illustrated as having the same size, shape, and orientation, in embodiments, any one or more of the size, shape, and orientation of protrusions 428 and 430 within a set, row, and/or column, may include any number of variances. Additionally, in embodiments, one or more of the protrusions 428 and/or 430 may have a same, similar, or different size and/or shape as any one or more of the protrusions 412 of the first set 410.

FIG. 4B is a side view of the IMD header 400 depicted in FIG. 4A, in accordance with embodiments of the disclosure. As shown in FIG. 4B, a second surface 417 of the header 400 may include a third set 436 of protrusions 438 and a fourth set 440 of protrusions 442. As shown, the third set 436 of protrusions 438 may be arranged in two rows perpendicular to the central axis 404 and the fourth set 440 of protrusions 442 may include two protrusions 442, each arranged at a different angle with respect to the central axis 404 (e.g., in a similar manner as the protrusions 428 and 430 are arranged). According to embodiments, the third and fourth sets 436 and 440, respectively, may include any number of protrusions arranged in any number of ways.

Figure 4C:
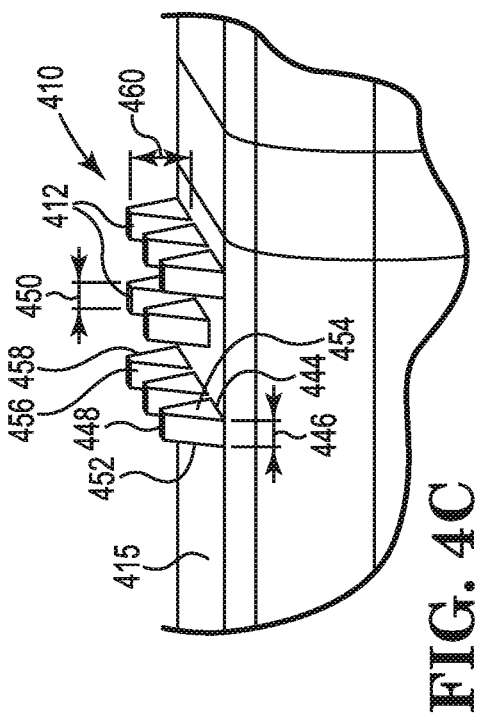
FIG. 4C is an expanded perspective view of a portion of the IMD header depicted in FIGS. 4A and 4B, in accordance with embodiments of the disclosure.

FIG. 4C is an expanded perspective view of a portion of the IMD header 400 depicted in FIGS. 4A and 4B, in accordance with embodiments of the disclosure, showing a close-up view of the first set 410 of protrusions 412. As shown, each of the protrusions 412 may have a truncated triangular prism shape. For example, each protrusion 412 may have a first base 444, having a width 446, attached to the first surface 415 of the IMD 402. Additionally, each of the protrusions 412 may have a narrower second base 448, having a width 450 that is less than the width 446 of the first base 444. In embodiments, the first base 444 and the second base 448 may each be at least approximately planar and, in embodiments, at least approximately parallel. A first pair of opposite sides 452 and 454 may extend between the first and second bases 444 and 448, and may be slanted, as shown. A second pair of opposite sides 456 and 458 may also extend between the first and second bases 444 and 448, and may be slanted, as shown. In embodiments, one or more of the sides 452, 454, 456, and 458 may not be slanted (e.g., may be oriented at least approximately perpendicular to the first surface 415), and/or may have a different angle of slant than one or more of the other sides 452, 454, 456, and 458.

The height 460 of each protrusion 412 may be sized to form a complementary fit to the teeth of a medical forceps (not shown). In embodiments, a length 462 of one or more protrusions 412 of the first set 410 may be less than, equal to, or greater than a length of one or more protrusions 428, 430 of the second set 426; the width of one or more of the bases 444 and 448 of one or more protrusions 412 of the first set 410 may be less than, equal to, or greater than a width of one or more of the bases of protrusions 428, 430 of the second set 426; and the height 460 of one or more protrusions 412 of the first set 410 may be less than, equal to, or greater than a height of one or more protrusions 428, 430 of the second set 426.

FIG. 5A is a top view of a header 500 of an IMD 502, in accordance with embodiments of the disclosure. The IMD 502 may be, be identical to, or be similar to, the IMD 102 depicted in FIG. 1, the IMD 200 depicted in FIGS. 2A and 2B, the IMD 300 depicted in FIG. 3, and/or the IMD 402 depicted in FIGS. 4A-4C. A central axis 504 of symmetry extends along the length of the IMD 502, and extending from a first end 506 of the header 500 to a second end 508, of the header 500, as shown.

A first set 510 of protrusions 512 is arranged, on a first surface 515 (which forms a portion of an outer surface of the IMD 502), near the second end 508 of the header 500. As shown in FIG. 5A, the first set 510 of protrusions 512 is arranged in four rows 514, 516, 518, and 520. Each row 514, 516, 518, and 520 includes one protrusion 512, and is oriented perpendicular to the central axis 504 and extends partially (and, in embodiments, at least approximately entirely) across a width 522 of the header 500, defined between a first side 524 and a second side 526. In other embodiments, one or more of the rows 514, 516, 518, and 520 may include more than one protrusion 512. Additionally, the first set 510 of protrusions 512 may include any number of rows and/or columns, any number of offset rows, and/or the like. Although all of the protrusions 512 of the first set 510 are illustrated as having the same size, shape, and orientation, in embodiments, any one or more of the size, shape, and orientation of protrusions 512 within a set, row, and/or column, may include any number of variances. For example, each of the protrusions 512 may have a truncated pyramid shape, a truncated triangular prism shape, a block shape, a cylindrical shape, and/or any other suitable three-dimensional shape. In the illustrated embodiments, and as also shown in FIG. 5B, there may be a space 532 defined between the rows of each set of adjacent rows 514, 516, 518, and 520. The space 532 may be sized to receive corresponding teeth of a medical forceps.

As shown in FIG. 5A, the header 500 includes a second set 528 of protrusions 530, arranged near the first end 506 of the header 500. Each of the protrusions 530 of the second set 528 is oriented at an angle to the central axis 504 of the IMD 502. As shown in FIG. 5A, the second set 528 of protrusions 530 includes two protrusions 530, each oriented at an angle to the other. In other embodiments, one or more of the protrusions 530 of the second set 528 may be parallel or perpendicular to the central axis 504 of the IMD 502. In embodiments, the second set 528 of protrusions 530 may include any number of protrusions, arranged in any number of different orientations, rows and/or columns, any number of offset rows, and/or the like. Additionally, each row and/or column of protrusions 530 of the second set 528 may include any number of protrusions 530 (e.g., one protrusion, two protrusions, three protrusions, four protrusions, etc.). Although both of the protrusions 530 of the second set 528 are illustrated as having the same size, shape, and orientation, in embodiments, any one or more of the size, shape, and orientation of protrusions 530 within a set, row, and/or column, may include any number of variances. Additionally, in embodiments, one or more of the protrusions 530 may have a same, similar, or different size and/or shape as any one or more of the protrusions 512 of the first set 510.

FIG. 5B is a side view of the IMD header 500 depicted in FIG. 5A, in accordance with embodiments of the disclosure. As shown in FIG. 5B, a second surface 517 of the header 500 may include a third set 534 of protrusions 536 and a fourth set 538 of protrusions 540. As shown, the third set 534 of protrusions 536 may be arranged in two rows perpendicular to the central axis 504 and the fourth set 538 of protrusions 540 may include two protrusions 540, each arranged at a different angle with respect to the central axis 504 (e.g., in a similar manner as the protrusions 530 are arranged). According to embodiments, the third and fourth sets 534 and 538, respectively, may include any number of protrusions arranged in any number of ways.

FIG. 5C is an expanded perspective view of a portion of the IMD header 500 depicted in FIGS. 5A and 5B, in accordance with embodiments of the disclosure, showing a close-up view of the first set 510 of protrusions 512. As shown, each of the protrusions 512 may have an elongated truncated pyramid shape. For example, each protrusion 512 may have a first base 544, having a width 546, that is attached to the first surface 515 of the IMD 502. Additionally, each of the protrusions 512 may have a narrower second base 548, having a width 550 that is less than the width 546 of the first base 544. In embodiments, the first base 544 and the second base 548 may each be at least approximately planar and, in embodiments, at least approximately parallel. A pair of opposite sides 552 and 554 may extend between the first and second bases 544 and 548, and may be slanted, as shown. A second pair of opposite sides 556 and 558 may also extend between the first and second bases 544 and 548, and may be slanted, as shown. In embodiments, one or more of the sides 552, 554, 556, and 558 may not be slanted (e.g., may be oriented at least approximately perpendicular to the first surface 515), and/or may have a different angle of slant than one or more of the other sides 552, 554, 556, and 558.

The height 560 of each protrusion 512 may be sized to form a complementary fit to the teeth of a medical forceps (not shown). In embodiments, a length 562 of one or more protrusions 512 of the first set 510 may be less than, equal to, or greater than a length of one or more protrusions 530 of the second set 528; the width of one or more of the bases 544 and 548 of one or more protrusions 512 of the first set 510 may be less than, equal to, or greater than a width of one or more of the bases of protrusions 530 of the second set 528; and the height 560 of one or more protrusions 512 of the first set 510 may be less than, equal to, or greater than a height of one or more protrusions 530 of the second set 528.

Embodiments of an IMD configured to be implanted within a patient's body (e.g., subcutaneously within an implantation location or pocket in the patient's chest or abdomen) and having protrusions coupled to an outer surface are described above. To reduce movement of the IMD, the protrusions placed on the outer surface of the IMD may be sized and arranged to allow a patient's tissue to be situated between the protrusions. In embodiments, the protrusions provide a structure that reduces at least one of rotational, translational, and lateral movement of the IMD within a patient's tissue after implantation in the patient. For example, having protrusions arranged at least partially across the width of an IMD may prevent longitudinal movement of the IMD within a patient's tissue, and having protrusions arranged at an angle to the central axis of the IMD may prevent the IMD from flipping or rotating within the patient's tissue. Additionally, having protrusions attached to the outer surface of the IMD may provide a structure that is complementary to the teeth of an insertion or extraction tool, giving a medical provider more control over the IMD while being held. For example, the protrusions may be sized and shaped to provide added frictional engagement with a medical forceps. The protrusions may make it easier for a heath care worker to grab the IMD with an extraction tool and remove the IMD from a patient without the IMD slipping from the extraction tool.

Figure 6:
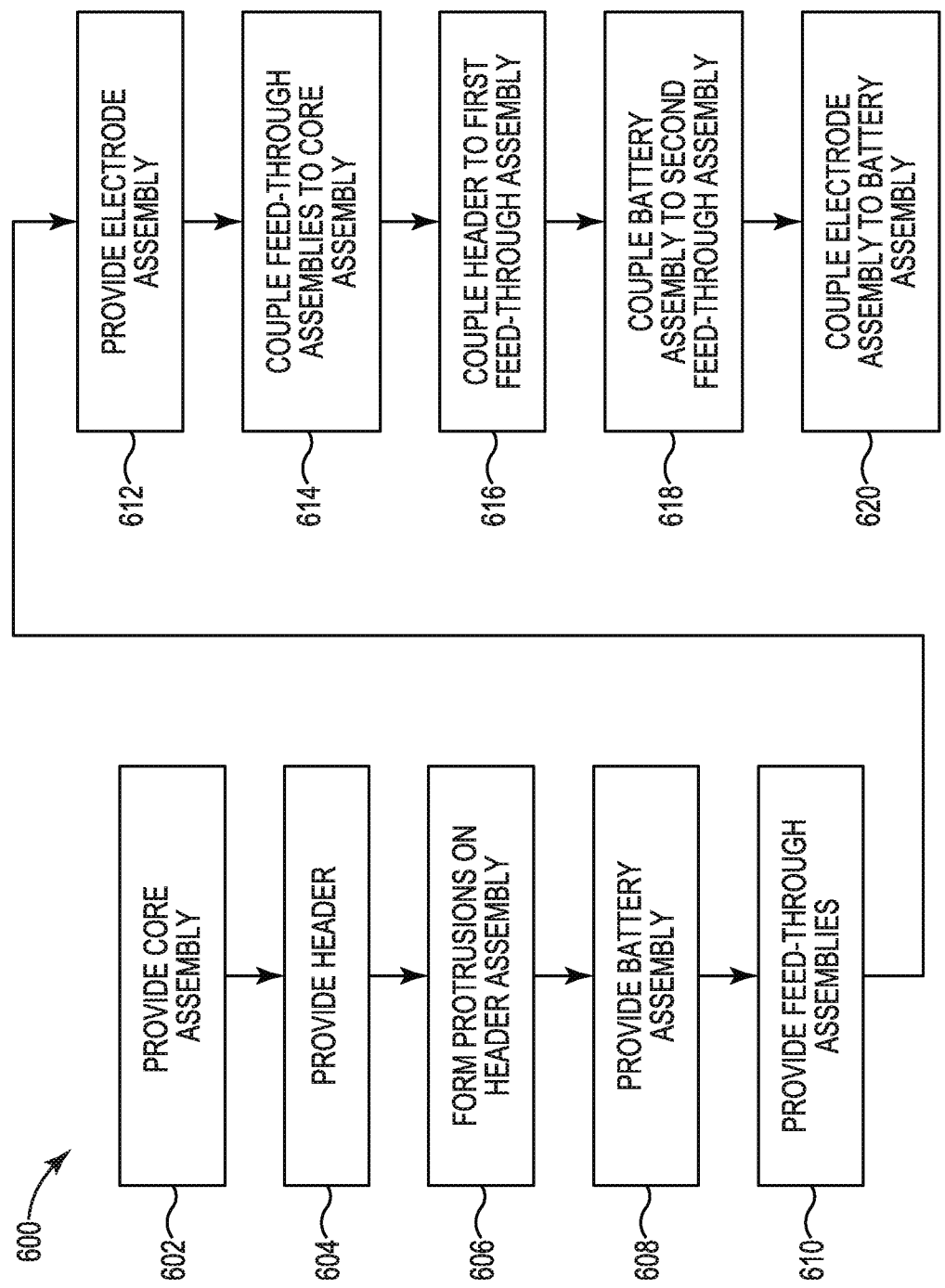
FIG. 6 is a flow diagram depicting an illustrative method of forming an IMD, in accordance with embodiments of the disclosure.

FIG. 6 is a flow diagram depicting an illustrative method 600 of manufacturing an IMD in accordance with embodiments of the disclosure. The IMD may be, for example, the IMD 102 depicted in FIG. 1, the IMD 200 depicted in FIGS. 2A-2B, the IMD 300 depicted in FIG. 3, the IMD 402 depicted in FIGS. 4A-4C, and/or the IMD 502 depicted in FIGS. 5A-5C. Embodiments of the method 600 include providing a core assembly (block 602), which may include obtaining and/or assembling one or more portions of a core circuitry assembly such as, for example, by assembling an integrated circuit, coupling circuitry to a liner, and/or the like, and enclosing the core circuitry assembly within a core assembly housing.

The method 600 also may include providing a header (block 604), which may include obtaining and/or assembling one or more portions of a header such as, for example, by arranging circuit components (e.g., an electrode and an antenna) on a scaffold assembly and enclosing the scaffold assembly within a header assembly housing. Protrusions are formed on the header assembly (block 606). In embodiments, for example, the header assembly housing may be formed from an epoxy, polymer, and/or the like, and may be formed by injection molding. The protrusions may be formed by designing the injection molds to include protrusions such that the protrusions are integrated into the structure of the header assembly housing. In other embodiments, the protrusions may be attached to the header assembly housing by other means such as, for example, by adhesion, welding, and/or the like. According to embodiments, protrusions may additionally, or alternatively, be formed on any number of other components (e.g., the core assembly housing, the battery assembly housing, and/or the electrode assembly housing).

The method 600 may also include providing a battery assembly (block 608) and providing feed-through assemblies (block 610), which may include obtaining and/or assembling a battery assembly and/or a first and second feed-through assembly. The method 600 may also include providing an electrode assembly (block 612), which may include forming an electrode that can be disposed on an outer surface of the battery assembly housing, forming an electrode that can be integrated within the battery assembly housing, forming an electrode assembly having a housing within which is disposed an electrode, and/or the like. As depicted in FIG. 6, embodiments of the method 600 also include coupling the feed-through assemblies to the core assembly (block 614), coupling the header to a first feed-through assembly (block 616), coupling the battery assembly to a second feed-through assembly (block 618), and coupling the electrode assembly to the battery assembly (block 620).

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An implantable medical device comprising:
   a core assembly housing having an outer surface;
   a header housing coupled to the core assembly housing, the header housing having a first outer surface and a second outer surface extending from a first header end to a second header end, wherein the first outer surface is opposite and parallel the second outer surface; and
   a plurality of protrusions arranged in a plurality of rows and disposed on and extending from the first outer surface of the header housing, wherein at least one protrusion of the plurality of protrusions has sides that extend from a base of the at least one protrusion to an edge of the at least one protrusion, wherein the edge is spaced apart from the first outer surface of the header housing, wherein the base has a width that extends along the first outer surface of the header, wherein the edge has a width that is less than the width of the base, wherein the plurality of protrusions are configured to be gripped by an extraction tool used to extract the implantable medical device from a tissue pocket by having spaces defined between each of the plurality of protrusions that are sized to receive corresponding teeth of the extraction tool, wherein a length of the edge is greater than the width of the edge, wherein each of the plurality of rows of protrusions is aligned parallel to a first axis, and wherein the first axis is perpendicular to a second axis, the second axis comprising an axis of symmetry of the header, extending from the first header end to the second header end; and
   an elongated protrusion oriented at an angle that is greater than zero degrees and less than ninety degrees relative to the second axis.

2. The implantable medical device of claim 1, each row extending at least partially across a width of the first side.

3. The implantable medical device of claim 2, the plurality of protrusions comprising at least one additional row of protrusions disposed on the second side.

4. The implantable medical device of claim 1, wherein each of the plurality of rows of protrusions is arranged to be offset from an adjacent row of protrusions.

5. The implantable medical device of claim 1, further comprising an elongated protrusion oriented at an angle to the second axis.

6. The implantable medical device of claim 1, wherein at least one protrusion of the plurality of protrusions has an elongated truncated pyramid shape.

7. The implantable medical device of claim 1, wherein at least one protrusion of the plurality of protrusions has a truncated triangular prism shape.

8. The implantable medical device of claim 1, wherein the plurality of protrusions are shaped to provide a complementary fit to a plurality of teeth of a medical forceps.

9. The implantable medical device of claim 1, wherein the protrusions are configured to reduce at least one of rotational, translational, and lateral movement of the implantable medical device within a patient's tissue after implantation in the patient.

10. An implantable medical device comprising:
    a core assembly comprising a core assembly housing, the core assembly having a first end and a second end;
    a header coupled at a first header end to the first end of the core assembly housing, the header comprising a header housing having a first outer surface and a second outer surface extending from the first header end to a second header end, wherein the first outer surface is opposite and parallel the second outer surface; and
    a plurality of protrusions arranged in a plurality of rows and disposed on the first outer surface of the header housing, wherein at least one of the plurality of protrusions has an elongated shape extending along a width of the first outer surface of the header housing for a greater distance than along a length of the first outer surface of the header housing, each of the plurality of protrusions extending partially across the width of the first outer surface of the header housing, wherein the plurality of protrusions are shaped to provide a complementary fit to a plurality of teeth of a medical forceps by having spaces defined between each of the plurality of protrusions that are sized to receive corresponding teeth of the medical forceps, wherein each of the plurality of rows of protrusions is aligned parallel to a first axis, and wherein the first axis is perpendicular to a second axis, the second axis comprising an axis of symmetry of the header, extending from the first header end to the second header end; and
    an elongated protrusion oriented at an angle that is greater than zero degrees and less than ninety degrees relative to the second axis.

11. The implantable medical device of claim 10, each row extending at least partially across a width of the first side.

12. A method of forming an implantable medical device, the method comprising:
    forming a core assembly comprising a core assembly housing, the core assembly having an outer surface extending between a first end and a second end;
    forming a header, the header comprising a header housing having a first outer surface and a second outer surface extending from a first header end to a second header end, wherein the first outer surface is opposite and parallel the second outer surface;
    forming a plurality of protrusions arranged in a plurality of rows and disposed on the first outer surface of the header housing, wherein at least one of the plurality of protrusions has sides that extend from a base of the at least one protrusion to an edge of the at least one protrusion, wherein the edge is spaced apart from the first outer surface of the header housing, wherein the base has a width that extends along the first outer surface of the header housing, wherein the edge has a width that is less than the width of the base, wherein the plurality of protrusions are configured to be gripped by an extraction tool used to extract the implantable medical device from a tissue pocket by having spaces defined between each of the plurality of protrusions that are sized to receive corresponding teeth of the extraction tool, wherein a length of the edge is greater than the width of the edge, wherein each of the plurality of rows of protrusions is aligned parallel to a first axis, and wherein the first axis is perpendicular to a second axis, the second axis comprising an axis of symmetry of the header, extending from the first header end to the second header end;
    forming an elongated protrusion oriented at an angle that is greater than zero degrees and less than ninety degrees relative to the second axis; and
    coupling the header, at a first header end, to the first end of the core assembly housing.

13. The method of claim 12, each row extending at least partially across a width of the first side.

14. The method of claim 13, wherein forming the plurality of protrusions further comprises forming an elongated protrusion oriented at an angle to the second axis.

15. The method of claim 12, wherein at least one protrusion of the plurality of protrusions has at least one of an elongated truncated pyramid shape and a truncated triangular prism shape.

16. The method of claim 12, wherein forming the plurality of protrusions comprises shaping the plurality of protrusions to provide a complementary fit to a plurality of teeth of a standard medical forceps.

* * * * *